United States Patent [19]

Wisniewski

[11] 4,219,531
[45] Aug. 26, 1980

[54] SMOKE DIFFUSING DEVICE

[76] Inventor: Gerald A. Wisniewski, 2050 N. 86th St., Wauwatosa, Wis. 53226

[21] Appl. No.: 961,953

[22] Filed: Nov. 20, 1978

[51] Int. Cl.$^2$ .......................... A61L 9/02; F04B 49/00
[52] U.S. Cl. .................................. 422/124; 417/411; 422/126
[58] Field of Search ...................... 417/411, 234, 424; 422/124, 126, 305, 306; D23/78

[56] References Cited

U.S. PATENT DOCUMENTS

| | | | |
|---|---|---|---|
| 1,108,053 | 8/1914 | Wiwi et al. | 417/411 |
| 1,969,756 | 8/1934 | Lowell | 422/124 |
| 3,647,323 | 3/1972 | Thomas | 417/411 X |
| 4,154,251 | 5/1979 | Doyel | 422/124 |

*Primary Examiner*—Richard E. Gluck
*Attorney, Agent, or Firm*—Thomas F. Kirby

[57] ABSTRACT

A smoke diffusing device for distributing aromatic smoke from burning material, such as tobacco, incense, or the like, throughout a room comprises a housing having a receptacle thereon for holding burning material, a fan chamber within the housing into which the smoke is drawn from the receptacle through an inlet passage and from which it is forcibly expelled to atmosphere through an outlet passage by a small switch-operated battery-powered motor-driven fan located in the fan chamber. The fan motor, battery, switch, and necessary electric wiring are removably mounted and detachably interconnected in a main chamber in the housing. The main chamber, fan chamber, inlet passage and receptacle are defined by a cylindrical bore extending inwardly of the housing, and one end of the bore is closed by a removable end cap on which the switch is mounted. A cup-shaped adapter removably mounted on the motor and engageable with a shoulder formed in the bore serves to seal the fan chamber from the main chamber, to support the motor in the main chamber, to ensure correct positioning of the motor and fan, and to protect the motor and other components in the main chamber from smoke contamination.

7 Claims, 8 Drawing Figures

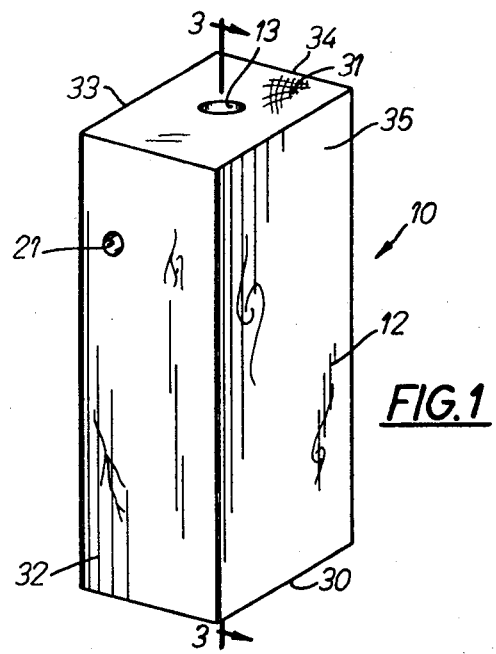
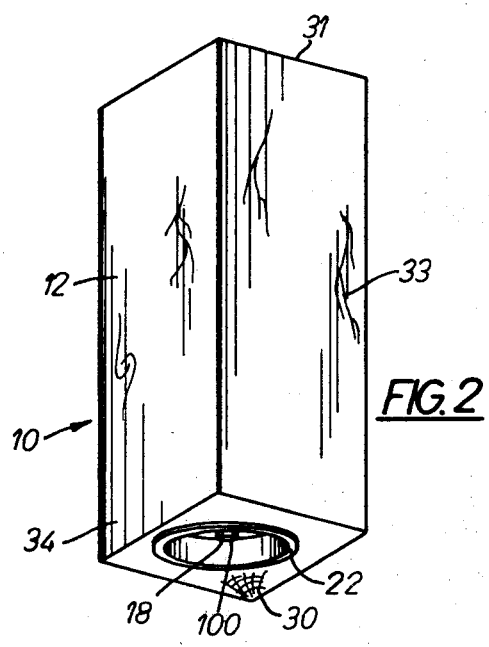
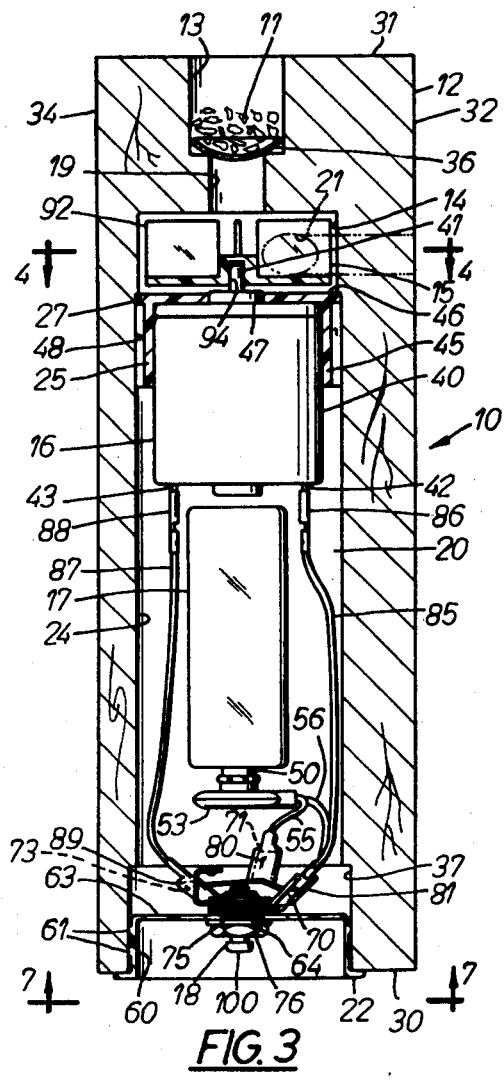
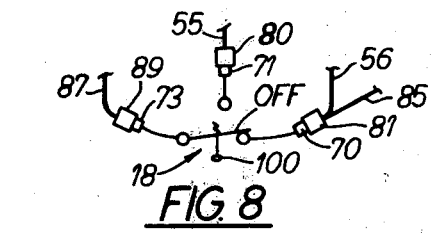
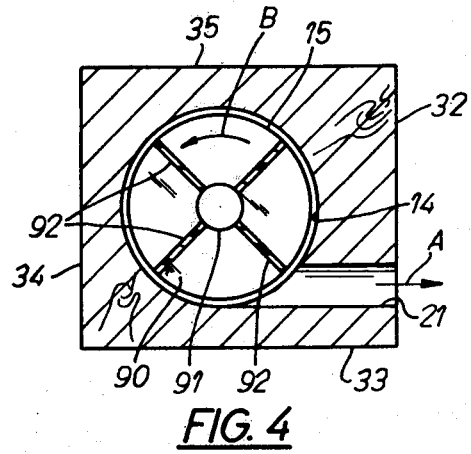

SMOKE DIFFUSING DEVICE

RELATED APPLICATION

This application relates to U.S. design patent application Ser. No. 841,759, filed Oct. 13, 1977, entitled "Smoke Diffusing Device" and owned by the same inventor as the present application.

FIELD OF INVENTION

This invention relates generally to smoke diffusing devices such as are used to distribute aromatic smoke from burning material, such as tobacco, incense, or the like, throughout a confined space, such as a room, for the benefit of occupants.

BACKGROUND OF PRIOR ART

Some smoke diffusing devices of the aforesaid character comprise a housing having a receptacle thereon for containing the burning material and a small switch-operated battery-powered motor-driven fan within the housing for diffusing the smoke from the receptacle throughout the room. In some prior art devices, the design, construction, and arrangement of the components thereof are such that assembly during manufacture is difficult, time consuming, and costly, smoke diffusion is not efficient, and ash, tars, resins, and other residue from the burning material and the smoke tend to cling to and clog the components and are not easily cleaned off.

SUMMARY OF PRESENT INVENTION

A smoke diffusing device in accordance with the invention comprises a housing having a receptacle on its top side for holding burning material, a fan chamber within the housing into which the smoke is drawn through an inlet passage and from which it is forcibly expelled to atmosphere through an outlet passage by a small switch-operated, battery-powered motor-driven fan located in the fan chamber. The fan motor, battery, switch, and necessary electric wiring are removably mounted and detachably interconnected in a main chamber in the housing. The main chamber, fan chamber, inlet passage, and receptacle are defined by a cylindrical bore extending inwardly from the bottom to the top of the housing, and the lower end of the bore is closed by a removable end cap on which the switch is mounted. The receptacle contains a removable screen on which the smoke-producing material burns. The upper part of the bore includes the fan chamber which is located below and connected to the receptacle by the smoke inlet passage. The fan chamber is connected to the smoke outlet passage through a side of the housing. The fan is disposed in the fan chamber and is removably mounted on and driven by the shaft of the cylindrical electric motor which is removably mounted in the main chamber of the bore. A cup-shaped adapter is removably mounted on the upper end of the motor and is engageable with a shoulder or abutment in the bore between the fan chamber and main chamber. The adapter serves to seal off the fan chamber from the main chamber, to support the motor in the main chamber, to protect the motor and other components in the main chamber against contaminants, and to ensure proper motor and fan positioning and location. The electric battery is located in the main chamber between the motor terminals and is electrically connectable thereto by detachable wire leads, also located in the main chamber, and detachably connected to an externally actuatable electric switch which is mounted on a removable end cap which seals the lower end of the bore. With combustible material burning in the receptacle, actuation of the switch energizes the motor and causes operation of the fan, thereby drawing smoke into the fan chamber for expulsion through the smoke outlet passage for diffusion into the atmosphere.

A smoke diffusing device of the present invention offers several advantages over the prior art. For example, construction of the housing, preferably made of wood, is very straightforward and economical, since the bore which serves numerous functions can be formed by very few drilling or boring operations. Furthermore, all components, except for the lower end cap are contained within the housing in a neat compact trouble-free arrangement. Furthermore, the adapter, which is mounted on the motor and cooperates with the shoulder in the bore, performs several functions, namely, effectively sealing off the smoke chamber, properly positioning the motor and attached fan within the bore, protecting the motor and components therebelow against contamination, and securely holding the motor in position. The fan is of such a size and construction relative to the fan chamber and the passages communicating therewith that smoke diffusion is highly efficient. Furthermore, all components are detachably mounted and interconnected thereby facilitating assembly during manufacture and disassembly for cleaning after use.

These and other objects of the invention will hereinafter appear.

BRIEF DESCRIPTION OF THE DRAWINGS

FIG. 1 is a perspective view taken from the upper side of a smoke diffusing device in accordance with the invention;

FIG. 2 is a perspective view taken from the lower side of the device of FIG. 1;

FIG. 3 is an enlarged cross-sectional view of the device taken on line 3—3 of FIG. 1;

FIG. 4 is a cross-sectional view of the fan blade in the housing taken on line 4—4 of FIG. 3;

FIG. 8 is a circuit diagram of the electrical system.

DESCRIPTION OF A PREFERRED EMBODIMENT

Figure 5:
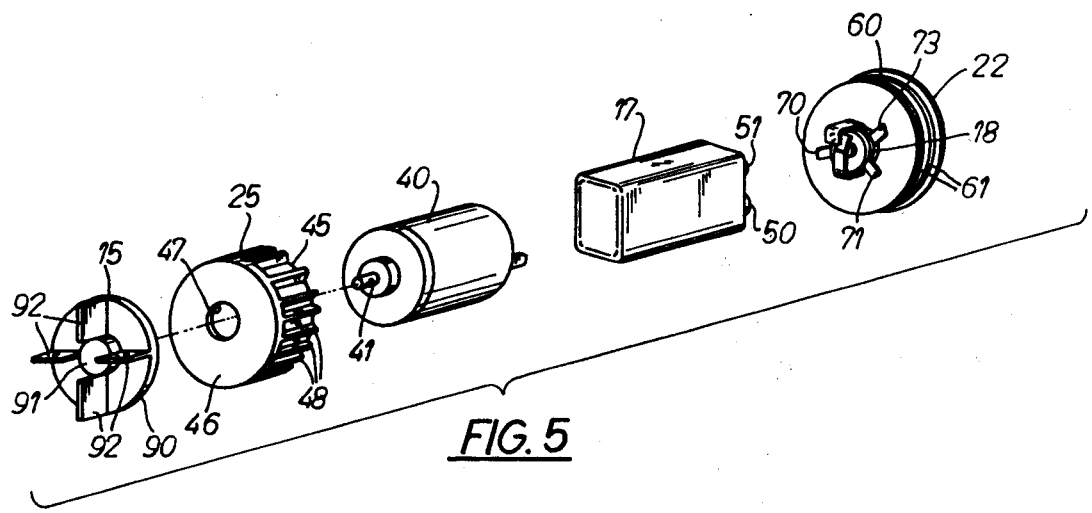
FIG. 5 is an exploded perspective view of the compartments of the device showing them removed from the housing.
Figure 6:
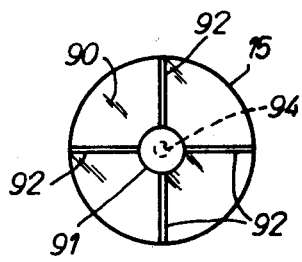
FIG. 6 is a top plan view of the fan blade shown in FIGS. 3 and 4.
Figure 7:
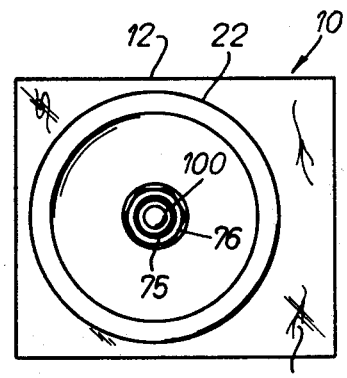
FIG. 7 is a bottom plan view of the adapter ring taken on line 7—7 of FIG. 3.

Referring to FIGS. 1, 2, and 3, the numeral 10 designates a smoke diffusing device, which is adapted to rest or stand on a table or other surface, for distributing aromatic smoke from burning material 11, such as tobacco, incense, or the like, throughout a room. Device 10 comprises a housing 12 having a receptacle 13 thereon for holding the burning material 11, a fan chamber 14 within the housing into which the smoke is drawn from the receptacle 13 through an inlet passage 19 and from which it is forcibly expelled to atmosphere through an outlet passage 21 (see arrow A in FIG. 4) by a small switch-operated battery-powered motor-driven fan 15 located in the fan chamber. A fan motor 16, a battery 17, a switch 18, and necessary electric wiring, hereinafter described, are removably mounted and detachably interconnected in a main chamber 20 in the housing 12. The main chamber 20, fan chamber 14, inlet passage 19 and receptacle 13 are defined by a cylindrical bore 24 extending inwardly of the housing 12, and one end of the bore is closed by a removable end cap 22 on which the switch 18 is mounted. A cup-shaped adapter 25 removably mounted on the motor 16 and engageable with a shoulder 27 formed in the bore 24 serves to seal the fan chamber 14 from the main chamber 20, to support the motor 16 in the main chamber, to ensure correct positioning of the motor 16 and fan 15, and to protect the motor and other components in the main chamber from smoke contamination.

Housing 12, which is preferably formed of wood (but could be plastic or metal), includes a bottom surface 30, a top surface 31, and side surfaces 32, 33, 34, and 35. Bore 24, which extends between bottom surface 30 and top surface 31 of housing 12, includes a recess 37 for receiving end cap 22, the main chamber 20, the fan chamber 14, the inlet passage 19, and the receptacle 13, each of progressively smaller diameter (except receptacle 13) and with chambers 20 and 14 defining the shoulder 27 therebetween. Bore 24 could be formed in one or several boring operations but receptacle 13 must be counter-bored since it is larger in diameter than inlet passage 19. Outlet passage 21 is bored through side surface 32 of housing 12.

Receptacle 13 contains a fine wire mesh metallic screen 36 in which the burning material 11 rests, which screen is removable for cleaning.

Motor 16 takes the form of a small commercially available direct current 9 volt motor having a cylindrical body 40. A rotatable motor drive shaft 41 extends from one end of the motor body 40 and a pair of laterally spaced apart positive and negative motor terminals 42 and 43, respectively, extend from the other end of the motor body 40. The diameter of motor body 40 is less than the diameter of main chamber 20 so that motor 16 is insertable therewithin during assembly and removable for cleaning.

The adapter 25, which is preferably formed of flexible plastic, is generally cup-shaped and comprises a cylindrical side wall 45 and an integrally formed flat end wall 46 which has a motor shaft hole 47 therethrough. Side wall 45 has a smooth interior surface which snugly engages motor body 40 and has spaced apart projections or ribs 48 on its exterior which slideably engage the wall of main chamber 20. End wall 46 engages or abuts against shoulder 27 to prevent movement of motor 16 therebeyond. Motor shaft 41 extends through shaft hole 47 in adapter 25 and extends into the fan chamber 14. Adapter 25 is snugly but slideably fitted on motor 16 and is insertable into and removable from the bore along with the motor. Thus, adapter 25 serves several functions: It seals main chamber 20 from fan chamber 14 against passage of smoke and residual substances thereby ensuring cleanliness of the components in the main chamber. It seals fan chamber 14 so that all fluid flow occurs without leakage between inlet passage 19 and outlet passage 21 thereby improving fan and fluid flow efficiency. It physically supports motor 16 frictionally within the bore, centers the motor, and automatically ensures correct axial positioning of the motor and its attached fan in the bore.

Battery 17 is a commercially available 9 volt direct current battery having positive and negative terminals 50 and 51, respectively, to which a commercially available removable snap-on connector 53 is attached, such connector having positive and negative insulated wire leads 55 and 56, respectively. Battery 17 physically fits between the motor terminals 42 and 43 to conserve space but is otherwise unsecured in the main chamber 20.

Removable end cap 22, which is preferably formed of flexible or resilient plastic, has a cylindrical portion 60 on which a plurality of annular projections 61 are externally formed to ensure that the cap fits tightly but removably in a friction fit in recess 37 of the bore 24 of the housing 12. Cap 22 includes an integrally formed end wall 63 having a switch-mounting hole 64 therethrough.

As FIGS. 3 and 8 show, switch 18 is a commercially available single pole double throw normally biased to shunt position-type switch. Switch 18 includes a pair of switch terminals 73 and 71 and a shunt terminal 70. Switch 18 also includes a threaded neck 75 which extends outwardly through hole 64 in cap 22 and which receives a nut 76 which secures the switch to the cap.

The wire leads 55 and 56 have connectors 80 and 81, respectively, which detachably engage the switch terminal 71 and the shunt terminal 70, respectively. Connector 81 is also connected to one end of an insulated wire lead 85 which has a connector 86 at its other end which detachably engages motor terminal 42. A wire lead 87 is provided and has connectors 89 and 88 at opposite ends which are detachably engaged with switch terminal 73 and motor terminal 43, respectively. Thus, actuation of switch 18 by depression of its pushbutton 100 connects switch terminal 73 to switch terminal 71 which causes energization of motor 16. Releasing pushbutton 100 to its shunt position connects shunt terminal 70 to switch terminal 73 which effects motor braking and deenergization of motor 16.

Fan 15, which is preferably fabricated of plastic, comprises a circular base plate 90 from one side of which an integrally formed central hub 91 and four equidistantly spaced integrally formed fan blades 92 extend. Base plate 90 and hub 91 have a motor shaft-receiving hole 94 therein by means of which the fan 15 is frictionally but removably mounted on the motor shaft 41.

Device 10 is initially assembled as follows, for example. Adapter 25 is placed on motor 16, after which the fan 15 is placed on motor shaft 41. Switch 18 is attached to cap 22. The connectors of wire leads hereinbefore described are preassembled to the wires and then attached to the appropriate terminals of the motor 16, battery 17, and switch 18. The subassembly including the motor 16, fan 15, and adapter 25 is slid into the large open end of bore 24 and pushed inward until adapter 25 engages shoulder 27. Then, the battery 17 is inserted into bore 24 between the motor terminals 42 and 43. The protruding wire leads are then inserted into bore 24, after which the cap 22 is pressed into recess 37 of the bore 24 thereby enclosing all components therewithin. Screen 33 is inserted in receptacle 13.

When assembled, device 10 is put to use, the material 11 is placed on screen 36 in receptacle 13 and ignited with a match or lighter. During combustion, device 10 is periodically lifted from the surface on which it rests and switch 18 is actuated by depressing its pushbutton 89 to cause energization of the motor 16 and rotation of fan 15. Rotation of fan 15 causes smoke to be drawn from receptacle 13 through smoke inlet passage 19 into fan chamber 14 from whence it is expelled to atmosphere through smoke outlet passage 21.

Device 10 can be disassembled for cleaning by removing and disengaging such components as necessary, such as the screen 33, the fan 15, and the adapter 25.

In an actual embodiment of the present invention, the fan chamber 14 was 1-11/32 inches in diameter and 9/16 of an inch in length. The inlet and outlet passages 19 and 21, respectively, communicating therewith were ⅜ and ¼ inches, respectively, in diameter. The fan 15 disposed in the fan chamber 14 was 1¼ inches in diameter and 7/16 of an inch in axial length. Thus, the clearance space between the outer edge of the fan blades and the wall of the fan chamber was on the order of 3/64 of an inch. The clearance space between the base of the fan 15 and the adapter 25 was 1/16 of an inch. The clearance space between the top edges of the fan blades 92 and the upper wall of the fan chamber 14 was 1/16 of an inch. These sizes and clearance spaces, with the fan operating at 6,000 rpm, result in very efficient smoke transfer.

As FIG. 4 shows, the fan 15 rotates counterclockwise (with respect to FIG. 4) in the direction of arrow B so that the incoming smoke from passage 19 first enters the region defined by the inner ends of the fan blades 92 and is expelled tangentially from the fan 15 through the outlet passage 21 which intersects the fan chamber 14 tangentially. Thus, the construction of the fan 15, its relatively close confinement within fan chamber 14, and its relative position with respect to inlet passage 19 and outlet passage 21 adds to the efficient intake and expulsion of smoke.

I claim:

1. A smoke diffusing device for distributing aromatic smoke from burning material, such as tobacco, incense, or the like, throughout a room comprising:
   a housing having a receptacle thereon for holding burning material;
   a main chamber in said housing;
   a fan chamber within said housing into which the smoke is drawn from said receptacle through an inlet passage in said housing and from which it is forcibly expelled to atmosphere through an outlet passage in said housing;
   a fan located in said fan chamber;
   a fan motor, battery, switch, and electric wiring removably located in said main chamber in said housing;
   a removable cap for closing said main chamber;
   and an adapter removably mounted on said motor and engageable with the walls of said main chamber to seal said fan chamber from said main chamber and to support said motor in said main chamber.

2. A device according to claim 1 wherein said switch is mounted on said cap.

3. A device according to claim 1 including a shoulder formed in said main chamber and engageable with said adapter to ensure predetermined positioning of the motor and fan.

4. A device according to claim 1 wherein said fan and motor are detachably interconnected.

5. A device according to claim 1 wherein said main chamber, fan chamber, inlet passage and receptacle are defined by a cylindrical bore extending inwardly of said housing, and one end of said bore is closed by said cap.

6. A smoke diffusing device for distributing aromatic smoke from burning material, such as tobacco, incense, or the like, throughout a room comprising:
   a housing having a receptacle thereon for holding burning material;
   a main chamber in said housing and including a shoulder formed in said main chamber;
   a fan chamber within said housing into which the smoke is drawn from said receptacle through an inlet passage in said housing and from which it is forcibly expelled to atmosphere through an outlet passage in said housing;
   a fan located in said fan chamber;
   a fan motor detachably connected to said fan, a battery, a switch, and electric wiring detachably interconnected and removably located in said main chamber in said housing;
   a removable cap for closing said main chamber, said switch being mounted on said cap;
   and an adapter removably mounted on said motor and engageable with said shoulder in said main chamber to seal said fan chamber from said main chamber, to support said motor in said main chamber, and to ensure predetermined positioning of said motor and fan.

7. A device according to claim 6 wherein said main chamber, fan chamber, inlet passage and receptacle are defined by cylindrical bore extending inwardly of said housing, and one end of said bore is closed by said cap.

* * * * *